US012089811B2

(12) United States Patent
Ogi et al.

(10) Patent No.: US 12,089,811 B2
(45) Date of Patent: Sep. 17, 2024

(54) DISTAL END UNIT OF ENDOSCOPE, AND ENDOSCOPE

(71) Applicant: OLYMPUS CORPORATION, Tokyo (JP)

(72) Inventors: Shun Ogi, Hino (JP); Daichi Kodama, Hachioji (JP); Hiroyuki Motohara, Hachioji-shi (JP)

(73) Assignee: OLYMPUS CORPORATION, Tokyo (JP)

( * ) Notice: Subject to any disclaimer, the term of this patent is extended or adjusted under 35 U.S.C. 154(b) by 439 days.

(21) Appl. No.: 17/401,821

(22) Filed: Aug. 13, 2021

(65) Prior Publication Data

US 2021/0369086 A1    Dec. 2, 2021

Related U.S. Application Data

(63) Continuation of application No. PCT/JP2019/011115, filed on Mar. 18, 2019.

(51) Int. Cl.
    *A61B 1/00*    (2006.01)
(52) U.S. Cl.
    CPC ...... *A61B 1/00096* (2013.01); *A61B 1/00009* (2013.01); *A61B 1/00114* (2013.01)
(58) Field of Classification Search
    CPC ............ A61B 1/05; A61B 1/051; A61B 1/053
    See application file for complete search history.

(56) References Cited

U.S. PATENT DOCUMENTS

| 10,136,803 | B1 | 11/2018 | Griffin | |
|---|---|---|---|---|
| 2003/0233024 | A1* | 12/2003 | Ando | A61B 1/00096 600/111 |
| 2004/0242963 | A1* | 12/2004 | Matsumoto | G02B 23/2423 600/176 |

(Continued)

FOREIGN PATENT DOCUMENTS

| CN | 106061350 A | 10/2016 |
|---|---|---|
| JP | 2000-295503 A | 10/2000 |

(Continued)

OTHER PUBLICATIONS

International Search Report dated Jun. 25, 2019 received in PCT/JP2019/011115.

*Primary Examiner* — Michael J Carey
*Assistant Examiner* — Stephen Floyd London
(74) *Attorney, Agent, or Firm* — Scully, Scott, Murphy & Presser, P.C.

(57) ABSTRACT

A distal end unit includes: an image pickup unit made using a wafer level optics technique; a distal end frame forming an external shape of an insertion portion, the distal end frame being constituted by a resin molded article; an image pickup unit containing room containing the image pickup unit in an interior of the distal end frame, the image pickup unit containing room including a first opening portion and a second opening portion that are continuously formed, the first opening portion being positioned on the distal end surface of the distal end frame, the second opening portion being positioned on a side surface of the distal end frame; and a filler having light blocking property, the image pickup unit containing room being filled with the filler, the filler forming the external shape of a distal end portion with the distal end frame.

20 Claims, 13 Drawing Sheets

(56) References Cited

U.S. PATENT DOCUMENTS

| | | |
|---|---|---|
| 2005/0123264 A1 | 6/2005 | Takahashi |
| 2009/0026372 A1* | 1/2009 | Hayashi .............. H01L 31/0203 |
| | | 250/338.4 |
| 2012/0232343 A1* | 9/2012 | Levy ..................... A61B 1/018 |
| | | 600/109 |
| 2013/0165752 A1 | 6/2013 | Chou |
| 2014/0221743 A1* | 8/2014 | Sugiyama ............ A61B 1/0676 |
| | | 600/109 |
| 2014/0330081 A1* | 11/2014 | Imai ..................... A61B 1/0008 |
| | | 600/129 |
| 2016/0287060 A1 | 10/2016 | Usuda et al. |
| 2017/0064249 A1 | 3/2017 | Kitano |
| 2017/0127915 A1* | 5/2017 | Viebach ................ A61B 1/018 |
| 2018/0317756 A1 | 11/2018 | Unsai |
| 2019/0298153 A1* | 10/2019 | Sato ................... A61B 1/00018 |

FOREIGN PATENT DOCUMENTS

| | | |
|---|---|---|
| JP | 2005-148250 A | 6/2005 |
| JP | 2007-288168 A | 11/2007 |
| JP | 2009-201762 A | 9/2009 |
| JP | 2016-190007 A | 11/2016 |
| JP | 2017-505154 A | 2/2017 |
| JP | 2017-046832 A | 3/2017 |
| JP | 2017-099856 A | 6/2017 |
| JP | 2017113417 A * | 6/2017 |
| JP | 2017-195962 A | 11/2017 |
| JP | 2018-120005 A | 8/2018 |
| WO | 2007/108419 A1 | 9/2007 |
| WO | 2015/082328 A1 | 6/2015 |
| WO | 2017/203593 A1 | 11/2017 |
| WO | 2017/212779 A1 | 12/2017 |

\* cited by examiner

DISTAL END UNIT OF ENDOSCOPE, AND ENDOSCOPE

CROSS REFERENCE TO RELATED APPLICATION

This application is a continuation application of PCT/JP2019/011115 filed on Mar. 18, 2019, the entire contents of which are incorporated herein by this reference.

BACKGROUND OF THE INVENTION

1. Field of the Invention

The present invention relates to a distal end unit of an endoscope that includes an image pickup unit in an interior, and the endoscope.

2. Description of the Related Art

Conventionally, in a medical field or an industrial field, an endoscope has been widely used, for observing sites for which it is difficult to directly perform visual observation, for example, for observing an interior of a living body or a structural object. The endoscope is formed such that the endoscope can be introduced from an exterior of the living body or the structural object to the interior, and is configured such that the endoscope can form an optical image or can pick up the optical image.

In the endoscope, a distal end portion provided at a distal end of an insertion portion is mainly made up of a distal end unit in which various functional components are provided in a rigid distal end frame. As the distal end frame of the distal end unit, in recent years, a distal end frame using a technique for a molded interconnect device (MID) has been proposed. For example, International Publication No. 2015/082328 discloses an endoscope head (the distal end unit of the endoscope) including a head body (distal end frame) constituted by a MID element in which a plurality of conduction paths are formed, at least one electronic device to which electric power is supplied through the conduction paths, and a camera module (image pickup unit).

SUMMARY OF THE INVENTION

A distal end unit of an endoscope according to an aspect of the present invention includes: an image pickup unit including an optical unit and an image pickup device that are integrally formed, the optical unit being constituted by a lens stack body, the image pickup unit being made using a wafer level optics technique; a distal end frame having a columnar shape, a distal end surface of the distal end frame and a part of an outer circumference surface of the distal end frame forming an external shape of a distal end portion of an insertion portion, the distal end frame being constituted by a resin molded article; an image pickup unit containing room containing the image pickup unit in an interior of the distal end frame, the image pickup unit containing room including a first opening portion and a second opening portion that are continuously formed, the first opening portion being positioned on the distal end surface of the distal end frame, the second opening portion being positioned on a side surface of the distal end frame; and a filler having light blocking property, the image pickup unit containing room being filled with the filler so that the filler covers an outer circumference of the image pickup unit, the filler forming the external shape of the distal end portion with the distal end frame.

Further, an endoscope according to an aspect of the present invention includes a distal end unit including: an image pickup unit including an optical unit and an image pickup device that are integrally formed, the optical unit being constituted by a lens stack body, the image pickup remit being made using a wafer level optics technique; a distal end frame having a columnar shape, a distal end surface of the distal end frame and a part of an outer circumference surface of the distal end frame forming an external shape of a distal end portion of an insertion portion, the distal end frame being constituted by a resin molded article; an image pickup unit containing room containing the image pickup unit in an interior of the distal end frame, the image pickup unit containing room including a first opening portion and a second opening portion that are continuously formed, the first opening portion being positioned on the distal end surface of the distal end frame, the second opening portion being positioned on a side surface of the distal end frame; and a filler having light blocking property, the image pickup unit containing room being filled with the filler so that the filler covers an outer circumference of the image pickup unit, the filler forming the external shape of the distal end portion with the distal end frame, and the insertion portion in which the distal end unit is provided.

DETAILED DESCRIPTION OF THE PREFERRED EMBODIMENTS

Figure 1:
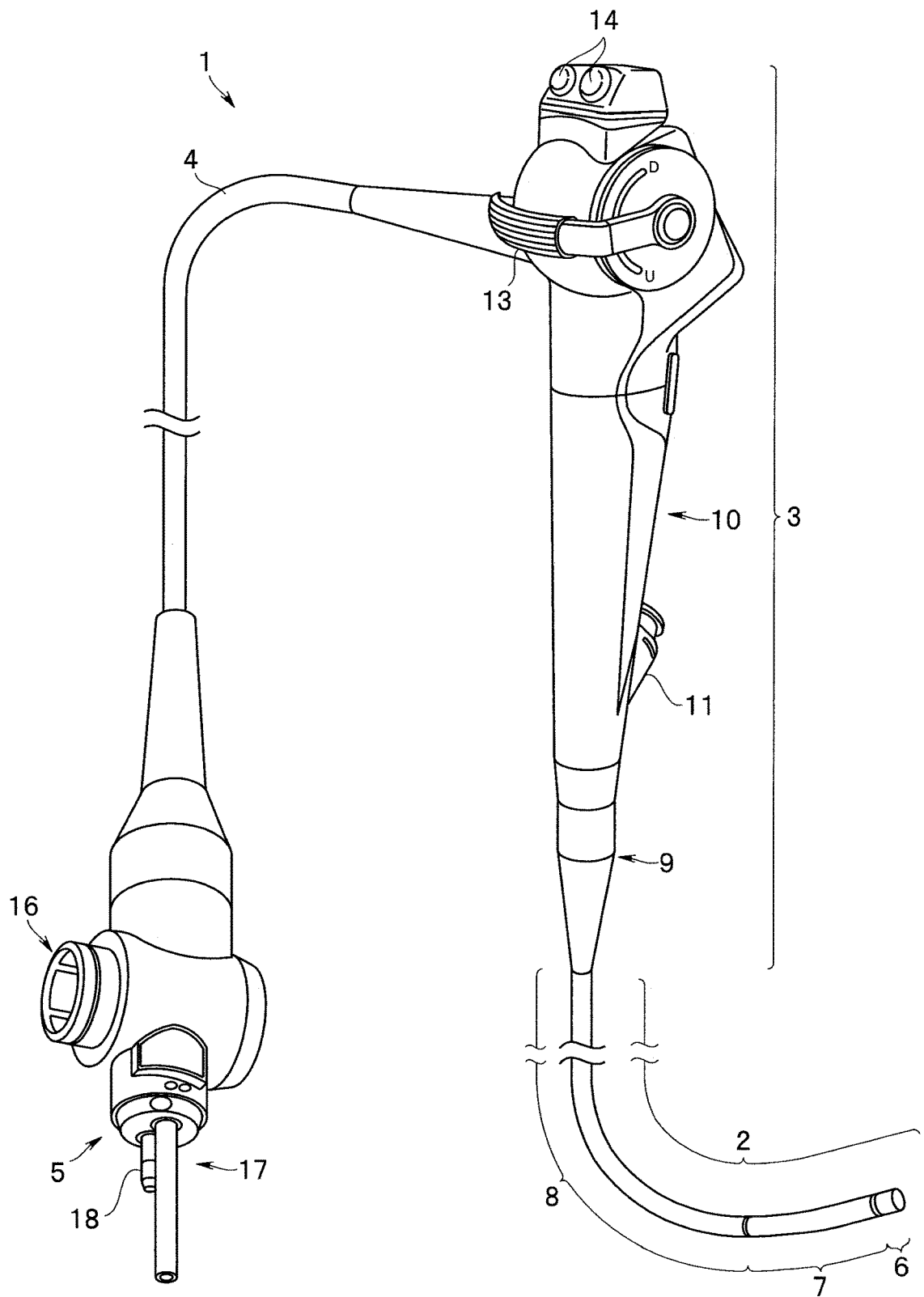
FIG. 1 is an external perspective view of an endoscope.

Embodiments of the present invention will be described below with reference to the drawings. FIG. 1 to FIG. 7 are diagrams according to a first embodiment, and FIG. 1 is an external perspective view of an endoscope.

An endoscope 1 shown in FIG. 1 is configured to include an elongated (long) insertion portion 2 that is inserted into a body cavity of a subject, an operation portion 3 that is provided so as to be continuous with a proximal end of the insertion portion 2, a universal cable 4 that extends from a proximal end of the operation portion 3, and an endoscope connector 5 that is arranged at an extension end of the universal cable 4.

The insertion portion 2 is a tubular member in which a distal end portion 6, a bending portion 7 and a flexible tube portion 8 are provided so as to be continuous in an order from a distal end side and that has flexibility.

Figure 2:
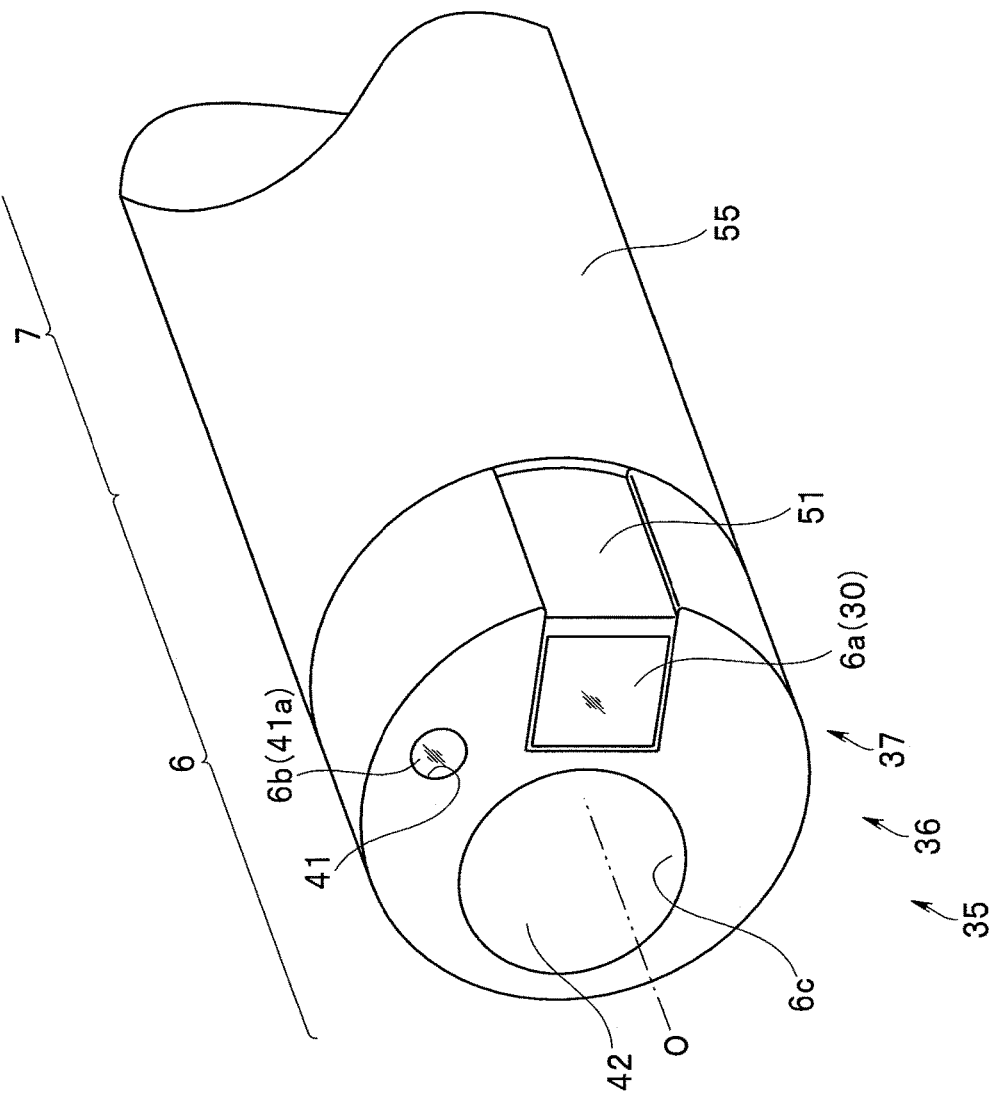
FIG. 2 is an external perspective view of a distal end portion.

As shown in FIG. 2, on a distal end surface of the distal end portion 6, for example, an observation window 6a for observing a subject, a pair of illumination windows 6b for emitting illumination light to the subject, and a channel opening portion 6c that communicates with a distal end side of a treatment instrument channel 27 are arranged.

Figure 3:
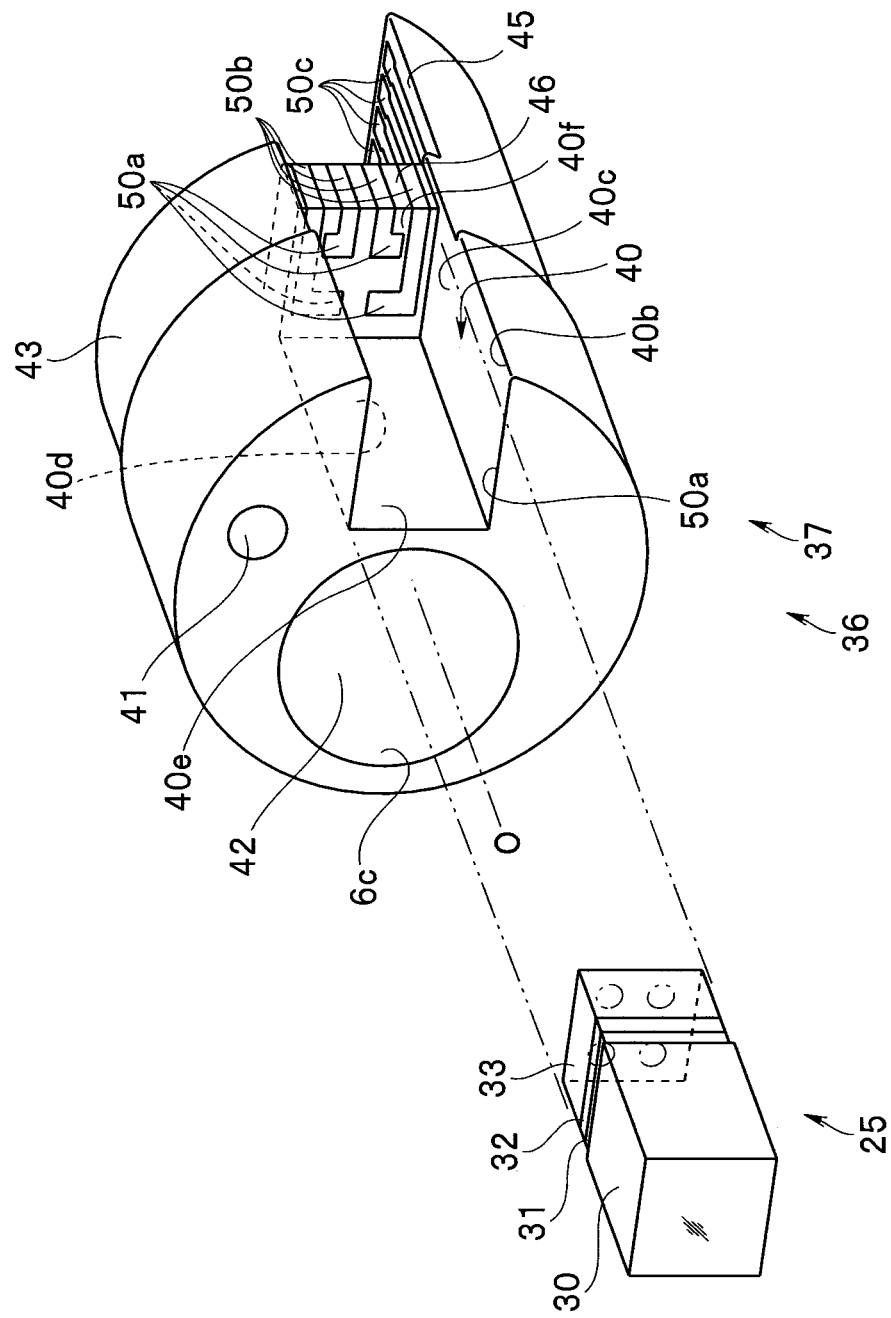
FIG. 3 is an exploded perspective view showing a distal end frame and an image pickup unit as viewed from a distal end side.
Figure 4:
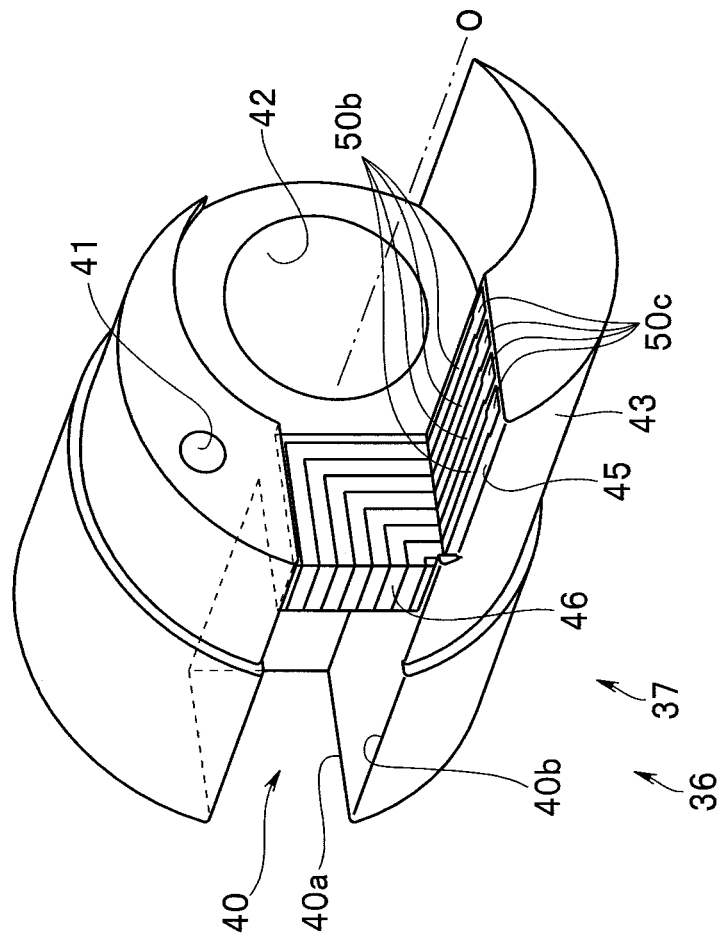
FIG. 4 is a perspective view showing the distal end frame as viewed from a proximal end side.
Figure 5:
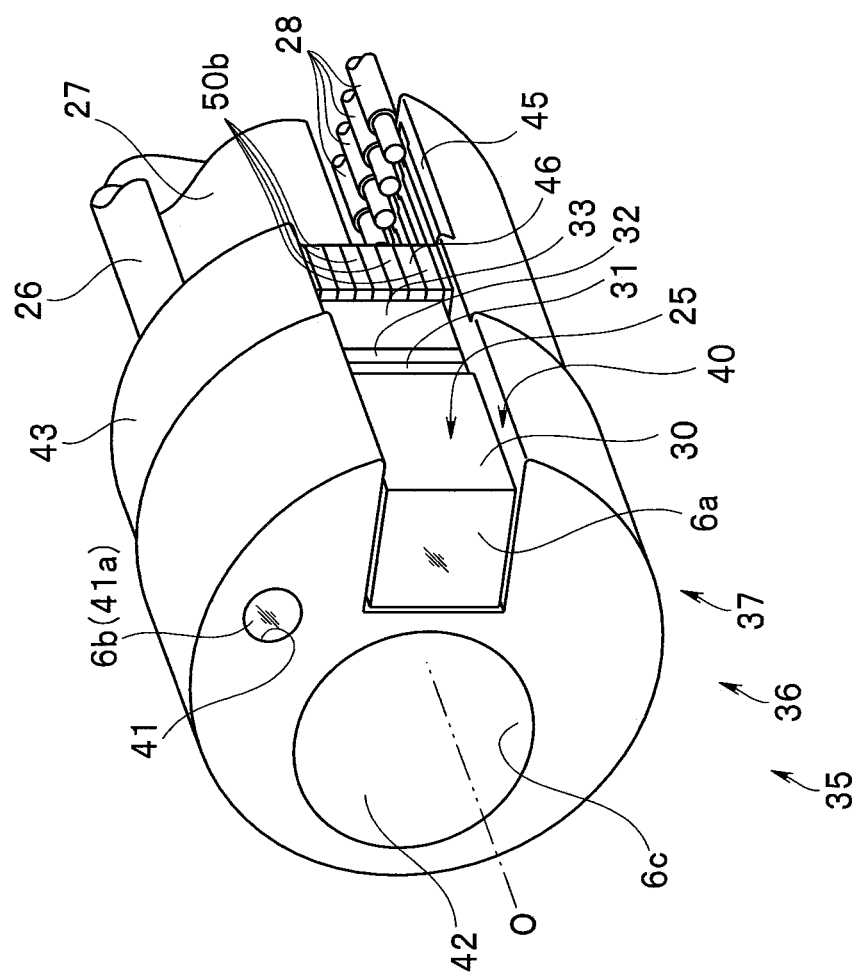
FIG. 5 is a perspective view showing a distal end unit before being filled with a filler as viewed from a distal end side.

As shown in FIG. 3 and FIG. 5, an image pickup unit 25, a distal end side of a light guide 26, and the like are arranged in an interior of the distal end portion 6. The image pickup unit 25 picks up an optical image of the subject, and the light guide 26 guides to the distal end portion 6 the illumination light to be emitted to the subject through the illumination window 6b.

For example, the bending portion 7 is a mechanism configured to actively bend in two bending directions of an upward direction and a downward direction (UP-DOWN). Note that an upward direction, a downward direction, a right direction and a left direction for the insertion portion 2 and the like are conveniently defined so as to correspond to an upward direction, a downward direction, a right direction and a left direction in an endoscope image that is picked up by the image pickup unit 25 in the embodiment.

The flexible tube portion 8 is a tubular member having flexibility and configured to be passively flexible. The light guide 26, the treatment instrument channel 27 and the like are inserted into an interior of the flexible tube portion 8, in addition to various cables 28 that are electrically connected to the image pickup unit 25 and the like.

The operation portion 3 is configured to include a bend preventing portion 9 that is connected to the flexible tube portion 8 so as to cover a proximal end of the flexible tube portion 8, and a grasping portion 10 that is provided so as to be continuous with a proximal end side of the bend preventing portion 9 and that can be grasped by user's hand.

A treatment instrument insertion portion 11 that communicates with a proximal end side of the treatment instrument channel 27 is provided on a distal end side of the grasping portion 10. Further, an operation lever 13 for performing a bending operation of the bending portion 7 and operation switches 14 to which various functions of the endoscope 1 are assigned are provided on a proximal end side of the grasping portion 10.

For example, the universal cable 4 is a composite cable that allows insertion of the various cables 28, the light guide 26 and the like in an interior thereof and that allows insertion of an air/water feeding tube (not illustrated) and the like in the interior thereof. The various cables 28 extend from the distal end portion 6 of the insertion portion 2, and a distal end side of the air/water feeding tube is connected to the treatment instrument channel 27.

The endoscope connector 5 is configured to include an electric connector portion 16 for connecting the various cables 28 to a video processor (not illustrated) that is an external apparatus, a light source connector portion 17 for connecting the light guide 26 to a light source apparatus (not illustrated) that is an external apparatus, and an air/water feeding plug 18 for connecting the air/water feeding tube to an air/water feeding apparatus (not illustrated) that is an external apparatus.

Next, a configuration of the distal end portion 6 will be more specifically described with reference to FIG. 2 to FIG. 6.

The distal end portion 6 in the embodiment is mainly made up of a distal end unit 35. In the distal end unit 35, various functional components such as an image pickup unit 25 are provided in a rigid distal end frame 36 constituted by a molded interconnect device (MID) and having a roughly circular columnar shape.

In the embodiment, the image pickup unit 25 is provided in the distal end frame 36 as a functional component. As shown in FIG. 3 and FIG. 5, for example, the image pickup unit 25 is configured by a CSP (chip size package) in which a lens unit 30 for image pickup, a cover glass 31, and an image pickup device 33 bonded to the cover glass 31 through an adhesion layer 32 are integrally packaged. The lens unit 30 for image pickup is constituted by a lens stack body made using a water level optics technique. The lens unit 30 for image pickup in the image pickup unit 25 is produced by making a plurality of lens wafers each of which a lens is formed on a base material such as a glass substrate and stacking and dicing the lens wafers, for example. Therefore, the lens unit 30 for image pickup in the embodiment is a lens unit that has a rectangular shape in planar view and that has no lens frame. Further, the image pickup device 33 also is formed in a rectangular shape in planar view, by dicing or the like, and the image pickup unit 25 in the embodiment has a roughly rectangular parallelepiped shape as a whole.

For example, the distal end frame 36 includes a distal end frame body 37 formed by injection molding using a resin material and having a roughly columnar shape (more specifically, a roughly circular columnar shape in the embodiment). In the distal end frame body 37, a distal end surface and a part of an outer circumference surface are exposed on a surface of the distal end portion 6, and directly form an external shape of the distal end portion 6. Therefore, as the resin material composing the distal end frame body 37, a material having not only compatibility with the MID technique but also biological compatibility is selected. In the embodiment, the distal end frame body 37 means a resin portion formed by injection molding, for example, and various wiring patterns and the like (described later) are formed on a surface of the distal end frame body 37 by metal patterns using the MID technique, so that the distal end frame 36 is provided.

In the distal end frame body 37, an image pickup unit containing room 40, a light source containing room 41 and a channel holding room 42 are formed. The image pickup unit containing room 40 serves as a containing room that contains the image pickup unit 25 that is an optical functional component. The light source containing room 41 serves as containing room that contains a distal end side of the light guide as a light source that is an optical functional component. The channel holding room 42 is a room for holding a distal end side of the treatment instrument channel 27.

A stepped portion is formed on an outer circumference of the distal end frame body 37, such that an outer diameter on the proximal end side is smaller than an outer diameter on the distal end side, and a smaller-diameter region on the proximal end side that is formed by the stepped portion is set as a fitting portion 43 that is connected to the bending portion 7 by fitting.

Furthermore, a cutout portion is provided on the fitting portion 43, and a plane formed by the cutout portion is set as a cable connection surface 45 for connecting various cables.

The image pickup unit containing room 40 is configured by a concave portion having a roughly rectangular shape with a first opening portion 40a and a second opening portion 40b. The first opening portion 40a is provided on the distal end surface of the distal end frame body 37, and the second opening portion 40b is provided on one side of the distal end frame body 37.

In other words, the first opening portion 40a positioned on the distal end surface of the distal end frame body 37 (the distal end frame 36) and the second opening portion 40b positioned on the side surface of the distal end frame body 37 are continuously formed in the image pickup unit containing room 40 in the embodiment.

As side surfaces that extend in a direction of an insertion axis O, the image pickup unit containing room 40 in the embodiment includes a first side surface 40c and a second side surface 40d that are provided so as to be continuous with the first opening portion 40a and the second opening portion 40b respectively, and a third side surface 40e that is provided so as to be continuous with the first opening portion 40a and that is provided so as to be continuous with the first side surface 40c and the second side surface 40d.

Further, the image pickup unit containing room 40 includes a proximal end surface that is provided so as to be continuous with proximal ends of the first to third side surfaces 40c, 40d, 40e and a proximal end of the second opening portion 40b, and the proximal end surface is set as a mounting surface 40f for mounting the image pickup unit 25.

On the mounting surface 40f, a plurality of (for example, four) first lands 50a are provided as metal patterns. The image pickup device 33 is electrically connected to each first land 50a by an electrically conductive material. Note that solder, an electrically conductive adhesive or the like can be suitably used as the electrically conductive material for electrically connecting the image pickup device 33 to the each first land 50a.

Furthermore, wiring patterns 50b as metal patterns are connected to the respective first lands 50a. Each wiring pattern 50b extends from the mounting surface 40f to the cable connection surface 45 through the side surface of the distal end frame body 37.

For example, as shown in FIG. 2 and FIG. 3, a communication groove 46 is provided on a side portion of the distal end frame body 37. The communication groove 46 communicates a part on a proximal end side of the image pickup unit containing room 40 to a region on a proximal end side of the distal end frame body 37 (namely, a region where the cable connection surface 45 is provided).

In the embodiment, the communication groove 46 is provided so as to be continuous with the proximal end of the second opening portion 40b. Further, each wiring pattern 50b extending from the side of the mounting surface 40f is arranged in the communication groove 46. Consequently, in the side portion of the distal end frame body 37, each wiring pattern 50b is arranged inside an inner circumference surface of the distal end frame body 37.

On the cable connection surface 45, second lands 50c as metal patterns are provided on proximal ends of the respective wiring patterns 50b. Further, signal cables 28 inserted into the insertion portion 2 are electrically connected to the respective second lands 50c by an electrically conductive material.

Each first land 50a, each wiring pattern 50b and each second land 50c are formed by the MID technique, and for example, are formed by activating a resin surface forming the distal end frame body 37 by laser irradiation or the like and then performing metal plating to the resin surface after the activation.

Figure 6:
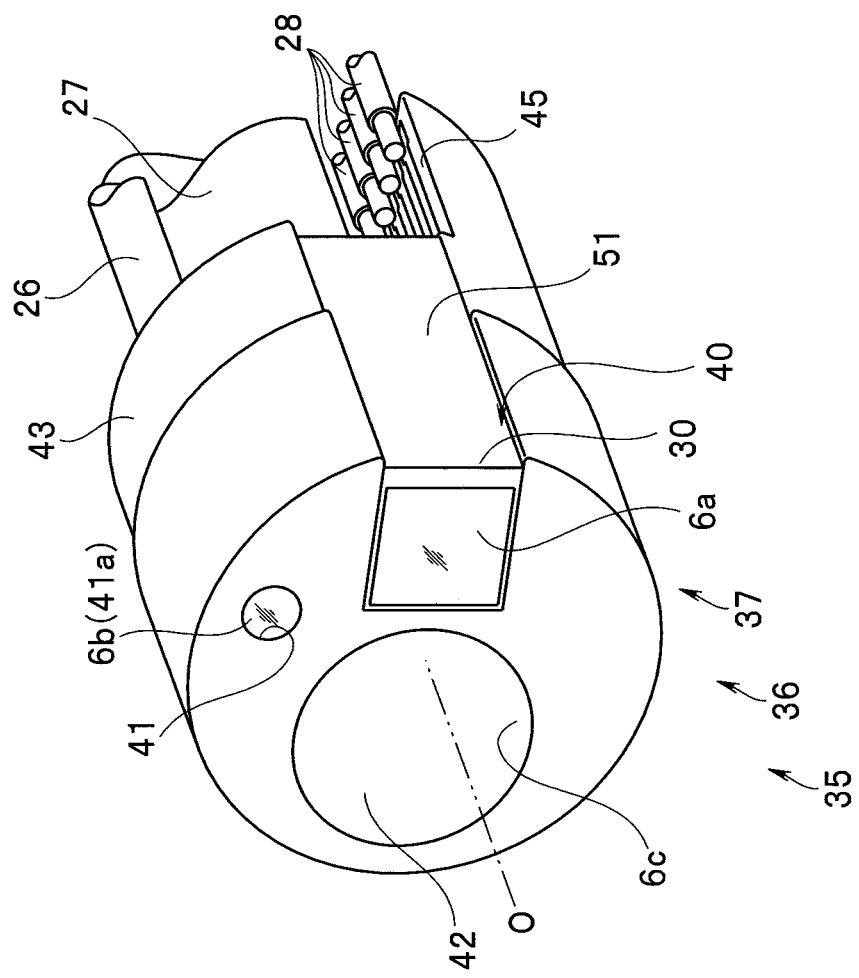
FIG. 6 is a perspective view showing the distal end unit as viewed from the distal end side.

As shown in FIG. 6, the image pickup unit containing room 40 that contains the image pickup unit 25 as described above is filled with a filler 51 having light blocking property. By the filler 51, an outer circumference of the image pickup unit 25 is covered, and an outer circumference of the lens unit 30 for image pickup is protected from light without using a shield member or the like. Furthermore, the communication groove 46 is also filled with the filler 51 integrally with the image pickup unit containing room 40. Consequently, in the side portion of the distal end frame body 37, each wiring pattern 50b is covered by the filler 51.

For example, the filling with filler is realized by dropping a filler fluid having a predetermined viscosity to the image pickup unit containing room 40 and the communication groove 46 and curing the filler fluid. In this case, widths of the image pickup unit containing room 40 and communication groove 46 are as small as about 0.5 mm to 1 mm, and therefore, the dropped filler fluid can be kept in interiors of the image pickup unit containing room 40 and the communication groove 46, by surface tension of the filler fluid. By curing the filler fluid kept in the interiors of the image pickup unit containing room 40 and the communication groove 46 in this way, a roughly flat surface of the filler 51 is formed on the side portion of the distal end frame body 37, without performing any special process. Parts of the surface formed on the side portion of the distal end frame body 37 by the filler 51 in this way are exposed on both surfaces of the distal end portion 6, and directly form the external shape of the distal end portion 6. Therefore, for the filler 51, a material having not only light blocking property but also biological compatibility is selected.

For example, the light source containing room 41 includes a through-hole that extends in the direction of the insertion axis O of the insertion portion 2. The light source containing room 41 is a circular hole in which a section shape in a direction orthogonal to the insertion axis O is a roughly circular shape.

The light guide 26 is inserted into the light source containing room 41. Furthermore, an optical member 41a such as an illumination lens or a cover glass is attached to the light source containing room 41, on the distal end side with respect to the light guide 26, and the optical member 41a closes a distal end side of the light source containing room 41, so that the illumination window 6b is formed on the distal end surface of the distal end frame 36.

The channel holding room 42 includes a through-hole that extends in the direction of the insertion axis O of the insertion portion 2. The channel holding room 42 is a circular hole in which a section shape in a direction perpendicular to the insertion axis O is a roughly circular shape.

The treatment instrument channel 27 is fixed to the channel holding room 42 by an unillustrated pipe sleeve. Further, a channel opening portion 6c is formed on the distal end side of the channel holding room 42.

On a proximal end side of the distal end unit 35 configured in this way, a cover member 55 having a tubular shape and configuring the bending portion 7 is connected to the fitting portion 43 by fitting. The cover member 55 is disposed such that a proximal end side covers a part of the filler 51 extending to the fitting portion 43, and is fixed to the fitting portion 43 and filler 51 by an adhesive or the like. Since the cover member 55 is fixed in this way, the proximal end side of the distal end unit 35 is sealed in a liquid-tight manner.

According to such an embodiment, it is possible to realize the reduction in the diameter of the distal end portion 6 while securing the optical performance of the image pickup unit 25, by configuring the distal end unit 35 including the image pickup unit 25 that is made using the water level optics technique and that has the lens unit 30, as an optical unit, constituted by the lens stack body and the image pickup device 33 integrally formed, the distal end frame 36 (the distal end frame body 37) that is constituted by a resin molded article and that has a columnar shape, the image pickup unit containing room 40 in which the first opening portion 40a positioned on the distal end surface of the distal end frame 36 and the second opening portion 40b positioned on the side surface of the distal end frame 36 are continuously formed and that contains the image pickup unit 25 in the interior of the distal end frame 36, and the filler 51 having light blocking property with which the image pickup unit containing room 40 is filled so that the filler 51 covers the outer circumference of the image pickup unit 25.

In other words, in the distal end portion 6 in the embodiment, the distal end frame 36 (the distal end frame body 37) constituted by the resin molded article is directly exposed to the exterior without being covered by a distal end cover or the like, and therefore, it is possible to realize the reduction in the diameter of the distal end portion 6 by a simple configuration.

Figure 7:
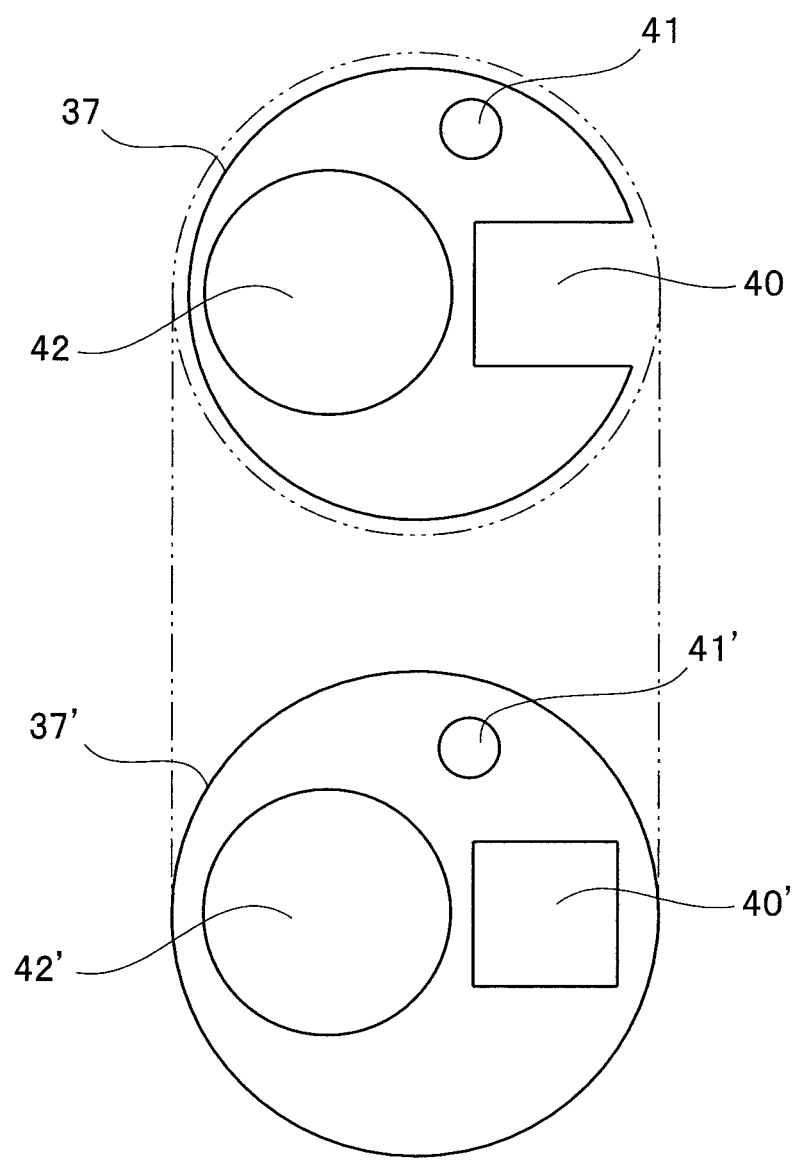
FIG. 7 is an explanatory diagram for comparing an outer diameter when an opening portion of an image pickup unit containing room is provided at a side portion of the distal end frame and an outer diameter when the opening portion is not provided.

In this case, for example, as shown in FIG. 7, compared to a distal end frame body 37' including an image pickup unit containing room 40', a whole circumference of which is surrounded by a wall surface, the distal end frame body 37 in the embodiment including the image pickup unit containing room 40 in which the opening portion 40b is formed on one side allows the reduction in outer diameter, because a thickness for forming the wall surface on the one side is unnecessary.

Further, since the image pickup unit 25 is made using the wafer level optics technique, it is possible to produce a small-size image pickup unit 25 at low cast, and this configuration can also contribute to the reduction in the diameter of the distal end portion 6.

In this case, the outer circumference of the lens unit 30 is not protected from light, because the lens unit 30 is cut out by dicing or the like. However, the image pickup unit containing room 40 is filled with the filler 51 having light blocking property, and the outer circumference of the image pickup unit 25 is covered by the filler 51. Accordingly, it is possible to secure the optical performance of the image pickup unit 25, without covering the image pickup unit 25 using a separate shield member or the like.

In addition, since the image pickup unit containing room 40 is filled with the filler 51, it is possible to strongly hold the image pickup unit 25 in the image pickup unit containing room 40.

Further, by configuring the distal end frame body 37 by the resin molded article having compatibility with the molded interconnect device and forming the first and second lands 50a, 50c and the wiring patterns 50b on the surface of the distal end frame body 37 by the MID technique, it is possible to easily realize the electric connection of the image pickup unit 25 to the signal cables 28 and the like, on the proximal end side of the distal end frame 36.

In this case, by providing the communication groove 46 communicating with the image pickup unit containing room 40 on the side surface of the distal end frame body 37 in the region of the distal end frame 36 that is on the proximal end side and where the cable connection surface 45 is provided and arranging the wiring patterns 50b in the region including the communication groove 46, it is possible to easily realize the wiring from the image pickup unit containing room 40 to the cable connection surface 45.

Furthermore, by also filling the filler 51 into the communication groove 46 integrally with the image pickup unit containing room 40, it is possible to adequately realize insulation of the wiring patterns 50b on the outer circumference of the distal end frame 36.

Figure 8:
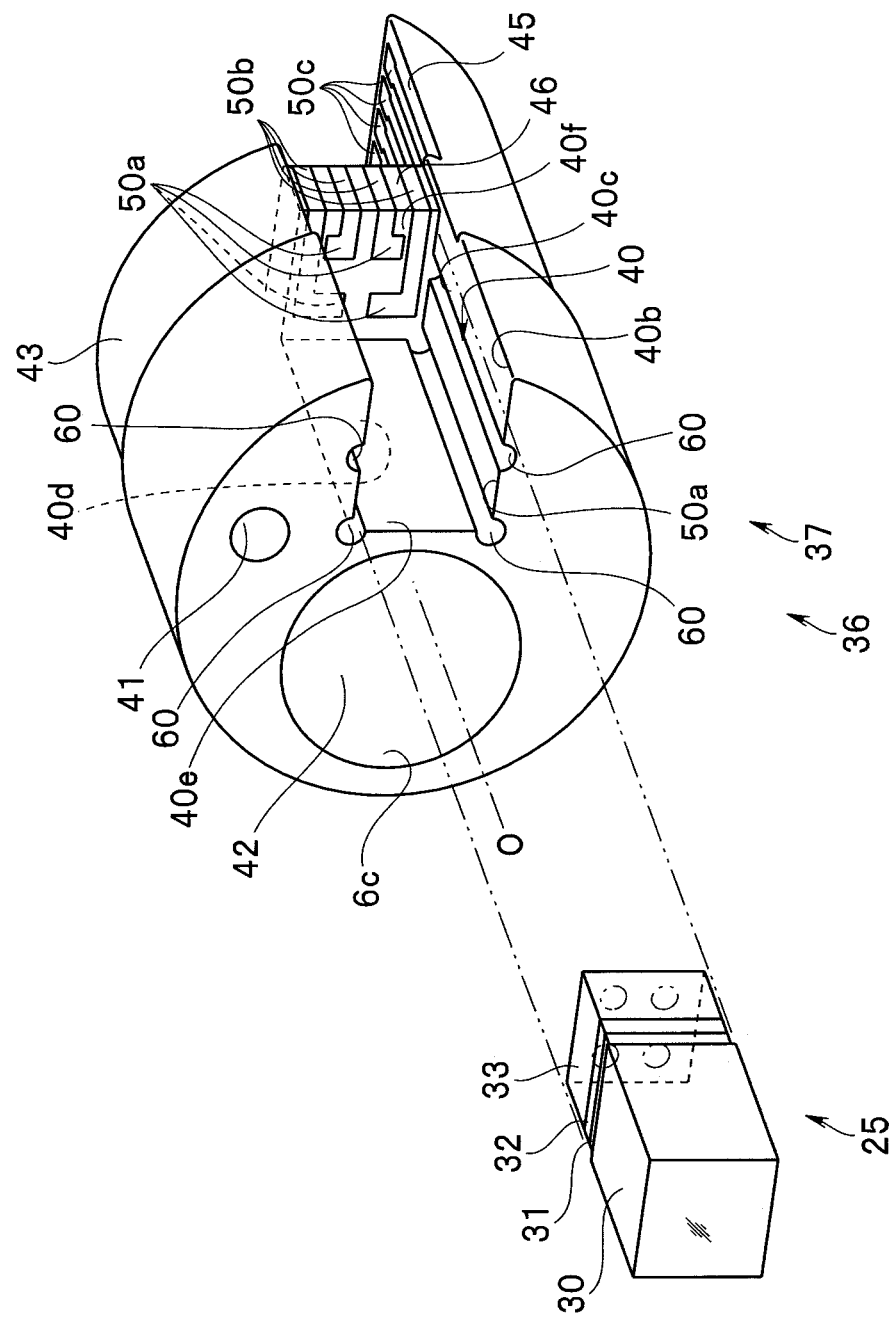
FIG. 8 is an exploded perspective view showing a distal end frame and an image pickup unit according to a first modification as viewed from the distal end side.
Figure 9:
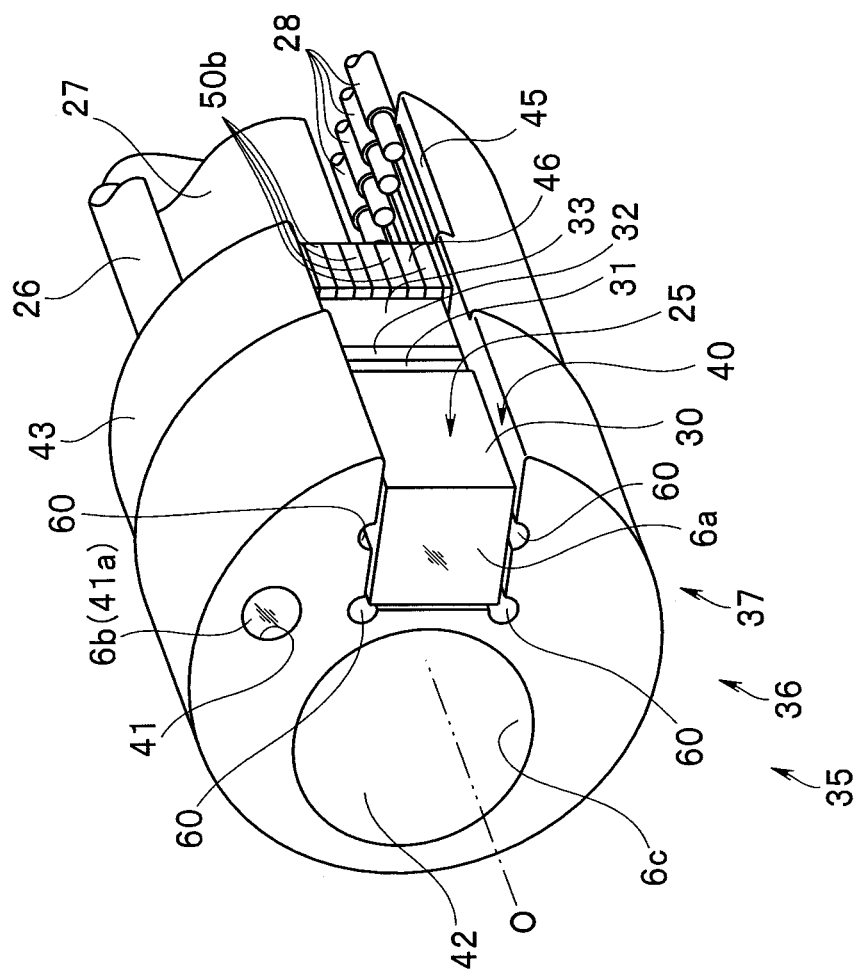
FIG. 9 is a perspective view showing a distal end unit before being filled with the filler according to the first modification as viewed from the distal end side.

For example, as shown in FIG. 8 and FIG. 9, grooves 60 extending in the direction of the insertion axis O can also be provided on a wall surface of the image pickup unit containing room 40.

By this configuration, it is possible to more adequately fill the image pickup unit containing room 40 with the filler 51.

In addition, by providing a groove 60 at each of a corner portion that is a connection region between the first side surface 40c and the third side surface 40e and a corner portion that is a connection region between the second side surface 40d and the third side surface 40e, it is possible to prevent interference between the image pickup unit containing room 40 and the image pickup unit 25 (see FIG. 9).

Figure 10:
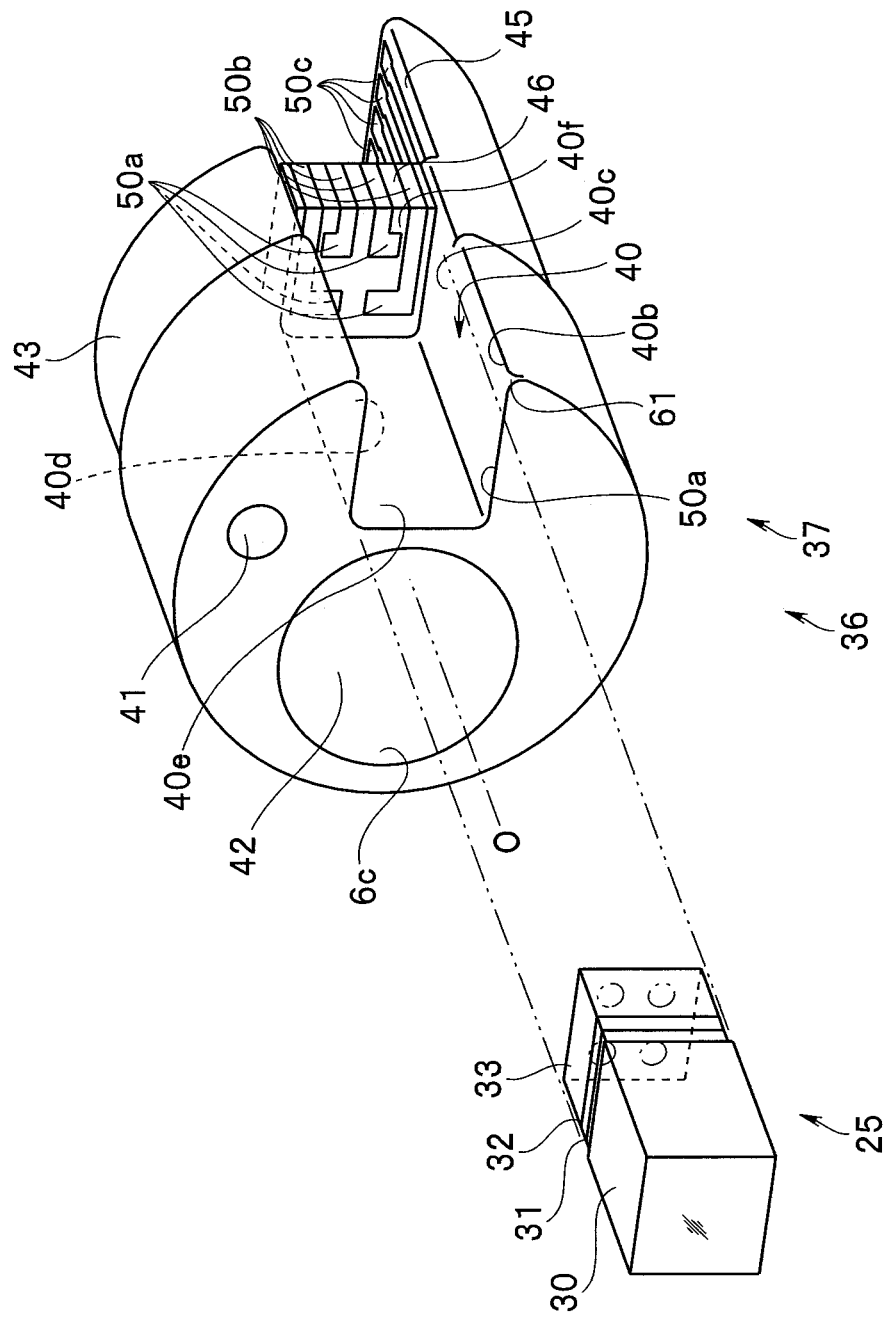
FIG. 10 is an exploded perspective view showing a distal end frame and an image pickup unit according to a second modification as viewed from the distal end side.

Further, for example, by forming a chamfered portion 61 at a corer portion between the first opening portion 40a and the second opening portion 40b as shown in FIG. 10, it is possible to prevent dripping using the surface tension of the filler fluid when the filler fluid fills the image pickup unit containing room 40.

Figure 11:
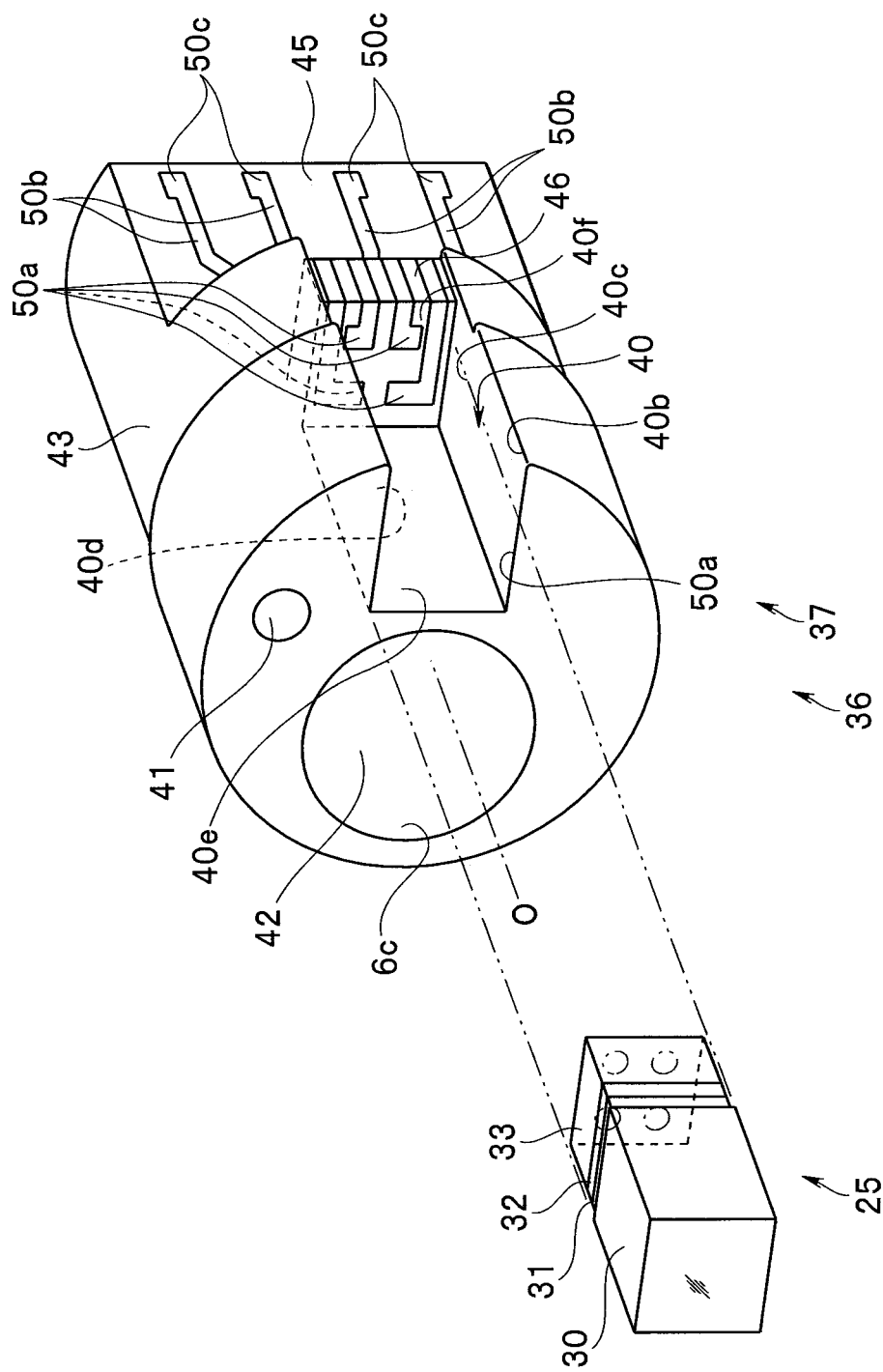
FIG. 11 is an exploded perspective view showing a distal end frame and an image pickup unit according to a third modification as viewed from a distal end side.
Figure 12:
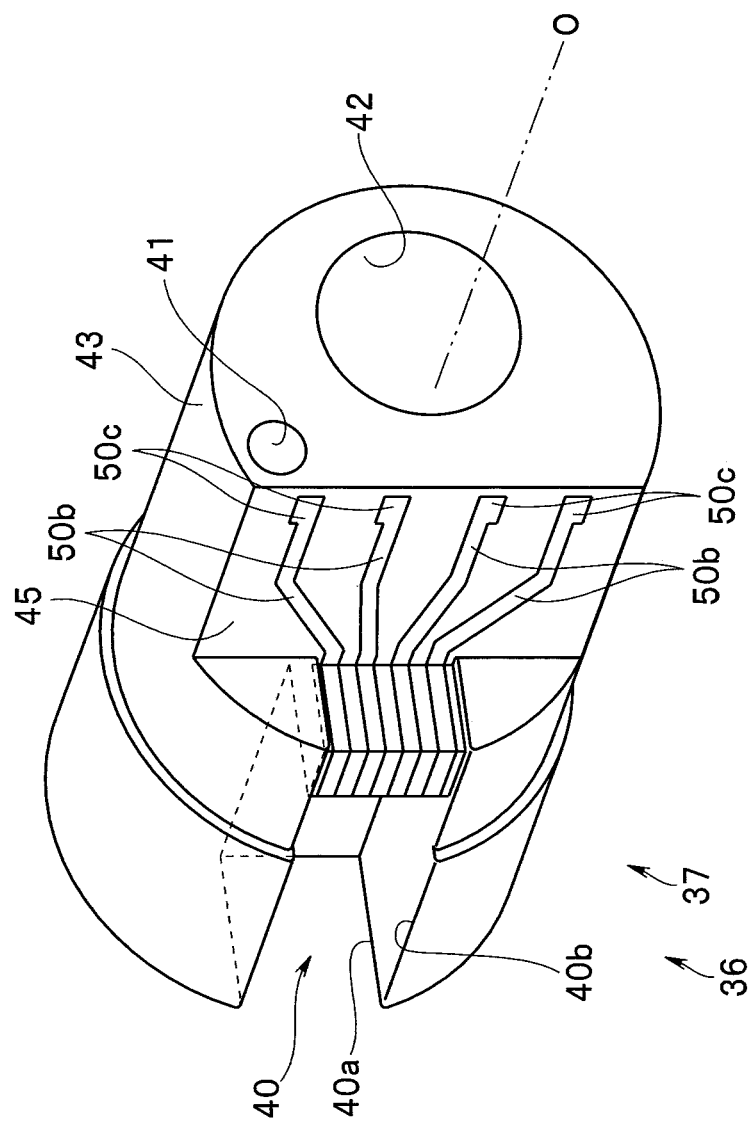
FIG. 12 is a perspective view showing the distal end frame according to the third modification as viewed from a proximal end side.

Further, for example, by forming the cable connection surface 45 such that the cable connection surface 45 is parallel to a bottom surface of the communication groove 46 as shown in FIG. 11 and FIG. 12, it is possible to secure a sufficiently wide cable connection surface 45, and it is possible to perform the electric connection of the signal cables 28 and the like to the second land 50c easily and adequately.

Figure 13:
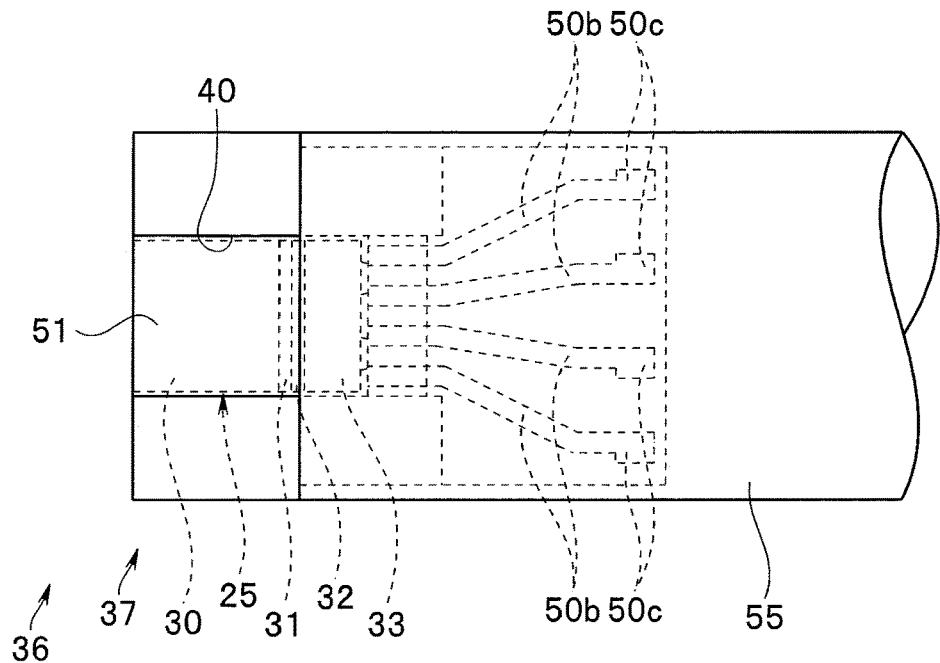
FIG. 13 is a plan view showing a principal part of a distal end portion according to the third modification.

For example, as shown in FIG. 13, it is preferable to set the position of the covering of the distal end frame 36 by the cover member 55, on the distal end side with respect to the image pickup unit 25, for adequately protecting the image pickup device 33 of the image pickup unit 25.

Figure 14:
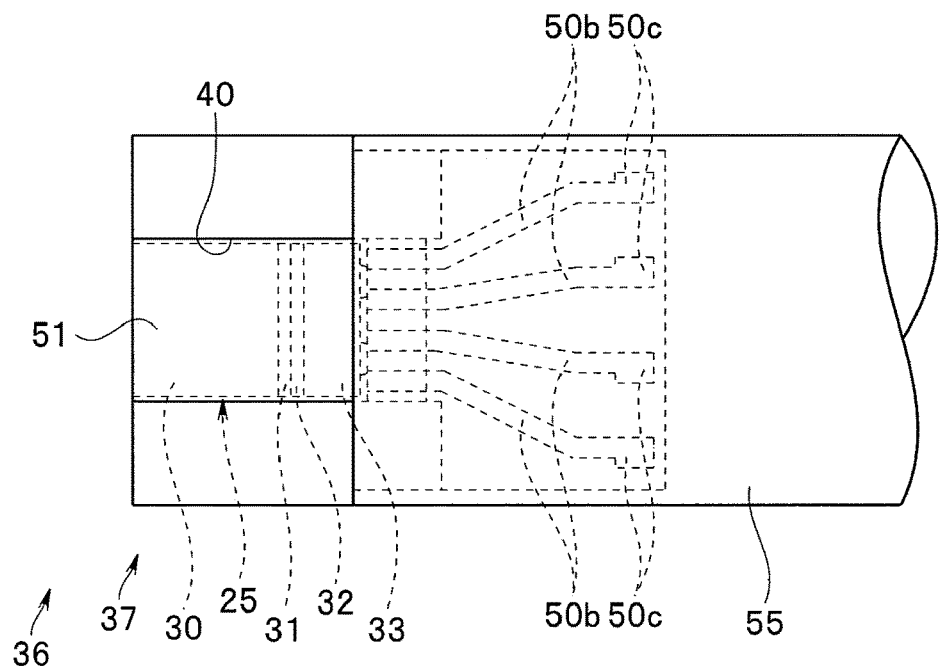
FIG. 14 is a plan view showing a principal part of a distal end portion according to a fourth modification.

Alternatively, for example, as shown in FIG. 14, it is allowable to set the position of the covering of the distal end frame 36 by the cover member 55, on the distal end side with respect to the connection portion between the image pickup device 33 and the first lands 50a, for adequately maintaining at least the electric connection state between the image pickup device 33 and the first lands 50a.

The present invention is not limited to the respective embodiments described above, various modifications and alterations can be made, and the modifications and alterations are included in the technical scope of the present invention. Needless to say, for example, components of the above-described embodiment and the respective modifications may be appropriately combined.

What is claimed is:
1. A distal end unit for use with an endoscope, the distal end unit comprising:
an image pickup unit including an optical unit and an image pickup device stacked in an optical axis direction, the optical unit comprising a lens stack body;

a distal end frame having a columnar shape, a distal facing surface of the distal end frame and a part of an outer circumference surface of the distal end frame forming a first portion of an external surface of a distal end portion that is configured to be exposed to a subject, the distal end frame comprising a resin molded article;

an image pickup unit containing room containing the image pickup unit in an interior of the distal end frame, the image pickup unit containing room including a first opening portion and a second opening portion that are continuously formed, the first opening portion being positioned on the distal facing surface of the distal end frame, the second opening portion being positioned on a side surface of the distal end frame; and a curable filler having light blocking property, the image pickup unit containing room being filled with the filler so that the filler covers an outer circumference of the image pickup unit, the filler directly forming a second portion of the external surface of the distal end portion that is configured to be exposed to the subject.

2. The distal end unit according to claim 1, wherein
the distal end frame makes up a molded interconnect device in which a metal pattern is formed on a surface of the resin molded article, and
the distal end frame further includes:
a first land provided in the image pickup unit containing room, the first land comprising the metal pattern electrically connected to the image pickup device;
a cable connection surface provided in the distal end frame on a proximal end side with respect to the image pickup unit containing room;
a second land comprising the metal pattern provided on the cable connection surface; and
a wiring pattern formed on the side surface of the distal end frame, the wiring pattern being comprising the metal pattern that electrically connects the first land and the second land.

3. The distal end unit according to claim 2, further comprising a communication groove provided at a side portion of the distal end frame so as to be continuous with the second opening portion, the communication groove communicating the image pickup unit containing room to a region of the distal end frame that is on the proximal end side and where the cable connection surface is provided, wherein
the wiring pattern is provided in a region that includes the communication groove.

4. The distal end unit according to claim 3, wherein
the communication groove is filled with the curable filler integrally with the image pickup unit containing room so that the filler covers the wiring pattern provided in the communication groove.

5. The distal end unit according to claim 2, wherein
the distal end frame includes a fitting portion on an outer circumference on the proximal end side, the fitting portion being configured to be fitted into a cover member having a tubular shape, and
when the fitting portion is fitted and fixed into the cover member, a connection portion between the first land and the image pickup device and the wiring pattern are covered by the cover member.

6. The distal end unit according to claim 1, wherein the image pickup unit containing room includes a first side surface and a second side surface that are provided so as to be continuous with the first opening portion and the second opening portion respectively, and a third side surface that is provided so as to be continuous with the first opening portion and that is provided so as to be continuous with the first side surface and the second side surface, and a groove is formed in each of a connection region between the first side surface and the third side surface and a connection region between the second side surface and the third side surface.

7. The distal end unit according to claim 6, wherein a corner portion between the first opening portion and the second opening portion is chamfered.

8. An endoscope comprising:
an insertion portion configured to be inserted into a subject, the insertion portion having an external surface configured to be exposed to the subject;
the insertion portion having a distal end unit disposed at a distal end of the insertion portion, the distal end unit including:
an image pickup unit including an optical unit and an image pickup device stacked in an optical axis direction, the optical unit comprising a lens stack body;
a distal end frame having a columnar shape, a distal end surface of the distal end frame and a part of an outer circumference surface of the distal end frame forming a portion of the external surface of the insertion portion, the distal end frame comprising a resin molded article;
an image pickup unit containing room containing the image pickup unit in an interior of the distal end frame, the image pickup unit containing room including a first opening portion and a second opening portion that are continuously formed, the first opening portion being positioned on the distal end surface of the distal end frame, the second opening portion being positioned on a side surface of the distal end frame; and
a curable filler having light blocking property, the image pickup unit containing room being filled with the filler so that the filler covers an outer circumference of the image pickup unit, the filler directly forming an other portion of the external surface of the insertion portion.

9. The endoscope according to claim 8, wherein
the distal end frame makes up a molded interconnect device in which a metal pattern is formed on a surface of the resin molded article, and
the distal end frame further includes:
a first land provided in the image pickup unit containing room, the first land comprising the metal pattern electrically connected to the image pickup device;
a cable connection surface provided in the distal end frame on a proximal end side with respect to the image pickup unit containing room;
a second land comprising the metal pattern provided on the cable connection surface; and
a wiring pattern formed on the side surface of the distal end frame, the wiring pattern being comprising the metal pattern that electrically connects the first land and the second land.

10. The endoscope according to claim 9, further comprising a communication groove provided at a side portion of the distal end frame so as to be continuous with the second opening portion, the communication groove communicating the image pickup unit containing room to a region of the distal end frame that is on the proximal end side and where the cable connection surface is provided, wherein
the wiring pattern is provided in a region that includes the communication groove.

11. The endoscope according to claim 10, wherein
the communication groove is filled with the curable filler integrally with the image pickup unit containing room so that the filler covers the wiring pattern provided in the communication groove.

12. The endoscope according to claim 9, wherein
the distal end frame includes a fitting portion on an outer circumference on the proximal end side, the fitting portion being configured to be fitted into a cover member having a tubular shape, and
when the fitting portion is fitted and fixed into the cover member, a connection portion between the first land and the image pickup device and the wiring pattern are covered by the cover member.

13. The endoscope according to claim 8, wherein the image pickup unit containing room includes a first side surface and a second side surface that are provided so as to be continuous with the first opening portion and the second opening portion respectively, and a third side surface that is provided so as to be continuous with the first opening portion and that is provided so as to be continuous with the first side surface and the second side surface, and a groove is formed in each of a connection region between the first side surface and the third side surface and a connection region between the second side surface and the third side surface.

14. The endoscope according to claim 13, wherein a corner portion between the first opening portion and the second opening portion is chamfered.

15. A distal end unit for use with an endoscope, the distal end unit comprising:
an image pickup unit including an optical unit and an image pickup device stacked in an optical axis direction, the optical unit comprising a lens stack body, the image pickup device having a plurality of contacts on a proximal face;
a distal end frame comprising a resin molded article and having a columnar shape, the distal end frame having a distal end face, a proximal end face, an outer circumferential surface, a proximal surface projecting proximally from the proximal end face and a channel forming a first opening on the distal end face and a second opening on the outer circumferential surface, the distal end frame having a wall at a proximal end of the channel, the wall having a first surface interior to the channel, a second surface disposed proximally relative to the first surface and a third surface connecting the first and second surfaces, the image pickup unit being disposed in the channel such that the proximal face faces the first surface;
a metal pattern formed on each of the first, second and third surfaces of the wall and on the proximal surface of the distal end frame, the metal pattern having first lands formed on the first surface corresponding to the plurality of contacts of the image pickup device and second lands formed on the proximal surface of the distal end frame, the metal pattern electrically connecting image pickup device to the second lands; and
a curable filler having light blocking property, the filler continuously covering the second opening and the third surface of the wall.

16. The distal end unit according to claim 15, wherein the third surface is recessed radially inward from the outer circumferential surface.

17. The distal end unit according to claim 15, wherein the channel has a pair of opposing side surfaces and a connecting surface connecting the pair of opposing side surfaces, the proximal surface being parallel to one or more of the pair of opposing side surfaces.

18. The distal end unit according to claim 15, wherein the channel has a pair of opposing side surfaces and a connecting surface connecting the pair of opposing side surfaces, the proximal surface being parallel to the connecting surface.

19. The distal end unit according to claim 15, wherein the channel has a pair of opposing side surfaces and a connecting surface connecting the pair of opposing side surfaces, and a groove is formed in a connection region between each of the pair of opposing side surfaces and the connecting surface.

20. The distal end unit according to claim 15, wherein the distal end frame has a first cylindrical portion and a second cylindrical portion disposed proximally relative to the first cylindrical portion, the second cylindrical portion having a second diameter smaller than a first diameter of the first cylindrical portion.

\* \* \* \* \*